United States Patent
Hossainy et al.

(10) Patent No.: US 9,248,034 B2
(45) Date of Patent: Feb. 2, 2016

(54) CONTROLLED DISINTEGRATING IMPLANTABLE MEDICAL DEVICES

(75) Inventors: Syed F. A. Hossainy, Fremont, CA (US); David C. Gale, San Jose, CA (US); Florian N. Ludwig, Mountain View, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 667 days.

(21) Appl. No.: 11/210,344

(22) Filed: Aug. 23, 2005

(65) Prior Publication Data

US 2007/0055364 A1 Mar. 8, 2007

(51) Int. Cl.
| | |
|---|---|
| *A61F 2/06* | (2013.01) |
| *A61F 2/82* | (2013.01) |
| *A61L 31/14* | (2006.01) |
| *A61L 31/16* | (2006.01) |
| A61F 2/91 | (2013.01) |

(52) U.S. Cl.
CPC ............. *A61F 2/82* (2013.01); *A61L 31/148* (2013.01); *A61L 31/16* (2013.01); *A61F 2/91* (2013.01); *A61F 2210/0004* (2013.01); *A61F 2250/0067* (2013.01); *A61L 2300/604* (2013.01); *A61L 2300/622* (2013.01)

(58) Field of Classification Search
CPC ............. A61F 2/82; A61F 2/86; A61F 2/91; A61F 2/92; A61F 2250/0067; A61F 2250/0068; A61F 2250/0059; A61F 2002/30062
USPC ............ 623/1.38, 1.42–1.44, 1.46–1.48, 1.15
See application file for complete search history.

(56) References Cited

U.S. PATENT DOCUMENTS

| | | |
|---|---|---|
| 3,687,135 A | 8/1972 | Stroganov et al. |
| 3,839,743 A | 10/1974 | Schwarcz |
| 3,900,632 A | 8/1975 | Robinson |
| 4,104,410 A | 8/1978 | Malecki |
| 4,110,497 A | 8/1978 | Hoel |
| 4,321,711 A | 3/1982 | Mano |
| 4,346,028 A | 8/1982 | Griffith |
| 4,596,574 A | 6/1986 | Urist |
| 4,599,085 A | 7/1986 | Riess et al. |
| 4,612,009 A | 9/1986 | Drobnik et al. |
| 4,633,873 A | 1/1987 | Dumican et al. |
| 4,656,083 A | 4/1987 | Hoffman et al. |

(Continued)

FOREIGN PATENT DOCUMENTS

| | | |
|---|---|---|
| DE | 44 07 079 | 9/1994 |
| DE | 197 31 021 | 1/1999 |

(Continued)

OTHER PUBLICATIONS

Freiberg et al. Polymer microspheres for controlled drug release. International Journal of Pharmaceutics 282 (2004) 1-18.*

(Continued)

*Primary Examiner* — Katherine Rodjom
(74) *Attorney, Agent, or Firm* — Squire Patton Boggs (US) LLP

(57) ABSTRACT

Implantable medical devices for treating bodily disorders local and distally to a region of implantation are disclosed. The devices include a body structure including an active agent, erodable particles acting as a carrier of the active agent, and an erodable binder. The binder releasably binds the particles together such that after implantation the binder erodes to release the particles.

22 Claims, 4 Drawing Sheets

(56) References Cited

U.S. PATENT DOCUMENTS

| | | |
|---|---|---|
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallstén et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,768,507 A | 9/1988 | Fischell et al. |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |
| 4,902,289 A | 2/1990 | Yannas |
| 4,977,901 A | 12/1990 | Ofstead |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,062,829 A | 11/1991 | Pryor et al. |
| 5,084,065 A | 1/1992 | Weldon et al. |
| 5,085,629 A | 2/1992 | Goldberg et al. |
| 5,100,429 A | 3/1992 | Sinofsky et al. |
| 5,104,410 A | 4/1992 | Chowdhary |
| 5,108,417 A | 4/1992 | Sawyer |
| 5,108,755 A | 4/1992 | Daniels et al. |
| 5,112,457 A | 5/1992 | Marchant |
| 5,123,917 A | 6/1992 | Lee |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,167,614 A | 12/1992 | Tessmann et al. |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,423,885 A | 6/1995 | Williams |
| 5,441,515 A | 8/1995 | Khosravi et al. |
| 5,443,458 A | 8/1995 | Eury et al. |
| 5,443,500 A | 8/1995 | Sigwart |
| 5,455,040 A | 10/1995 | Marchant |
| 5,464,650 A | 11/1995 | Berg et al. |
| 5,502,158 A | 3/1996 | Sinclair et al. |
| 5,514,379 A | 5/1996 | Weissleder et al. |
| 5,527,337 A | 6/1996 | Stack et al. |
| 5,545,408 A | 8/1996 | Trigg et al. |
| 5,554,120 A | 9/1996 | Chen et al. |
| 5,556,413 A | 9/1996 | Lam |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,605,696 A | 2/1997 | Eury et al. |
| 5,607,442 A | 3/1997 | Fischell et al. |
| 5,607,467 A | 3/1997 | Froix |
| 5,618,299 A | 4/1997 | Khosravi et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,651,976 A * | 7/1997 | Price et al. .................. 424/409 |
| 5,667,767 A | 9/1997 | Greff et al. |
| 5,667,796 A | 9/1997 | Otten |
| 5,670,558 A | 9/1997 | Onishi et al. |
| 5,693,085 A | 12/1997 | Buirge et al. |
| 5,700,286 A | 12/1997 | Tartaglia et al. |
| 5,707,385 A | 1/1998 | Williams |
| 5,711,763 A | 1/1998 | Nonami et al. |
| 5,716,981 A | 2/1998 | Hunter et al. |
| 5,725,549 A | 3/1998 | Lam |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,881 A | 4/1998 | Patnaik |
| 5,756,457 A | 5/1998 | Wang et al. |
| 5,756,476 A | 5/1998 | Epstein et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,780,807 A | 7/1998 | Saunders |
| 5,800,516 A | 9/1998 | Fine et al. |
| 5,811,447 A | 9/1998 | Kunz et al. |
| 5,824,049 A | 10/1998 | Ragheb et al. |
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohthuki et al. |
| 5,855,618 A | 1/1999 | Patnaik et al. |
| 5,858,746 A | 1/1999 | Hubbell et al. |
| 5,865,814 A | 2/1999 | Tuch |
| 5,868,781 A | 2/1999 | Killion |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |
| 5,877,263 A | 3/1999 | Patnaik et al. |
| 5,879,713 A | 3/1999 | Roth et al. |
| 5,888,533 A | 3/1999 | Dunn |
| 5,891,192 A | 4/1999 | Murayama et al. |
| 5,897,955 A | 4/1999 | Drumheller |
| 5,906,759 A | 5/1999 | Richter |
| 5,914,182 A | 6/1999 | Drumheller |
| 5,916,870 A | 6/1999 | Lee et al. |
| 5,922,005 A | 7/1999 | Richter et al. |
| 5,942,209 A | 8/1999 | Leavitt et al. |
| 5,948,428 A | 9/1999 | Lee et al. |
| 5,954,744 A | 9/1999 | Phan et al. |
| 5,957,975 A | 9/1999 | Lafont et al. |
| 5,965,720 A | 10/1999 | Gryaznov et al. |
| 5,971,954 A | 10/1999 | Conway et al. |

(56) References Cited

U.S. PATENT DOCUMENTS

| | | |
|---|---|---|
| 5,976,182 A | 11/1999 | Cox |
| 5,980,564 A | 11/1999 | Stinson |
| 5,980,928 A | 11/1999 | Terry |
| 5,980,972 A | 11/1999 | Ding |
| 5,981,568 A | 11/1999 | Kunz et al. |
| 5,986,169 A | 11/1999 | Gjunter |
| 5,997,468 A | 12/1999 | Wolff et al. |
| 6,010,445 A | 1/2000 | Armini et al. |
| 6,015,541 A | 1/2000 | Greff et al. |
| 6,042,875 A | 3/2000 | Ding et al. |
| 6,048,964 A | 4/2000 | Lee et al. |
| 6,051,648 A | 4/2000 | Rhee et al. |
| 6,056,993 A | 5/2000 | Leidner et al. |
| 6,060,451 A | 5/2000 | DiMaio et al. |
| 6,066,156 A | 5/2000 | Yan |
| 6,071,266 A | 6/2000 | Kelley |
| 6,074,659 A | 6/2000 | Kunz et al. |
| 6,080,177 A | 6/2000 | Igaki et al. |
| 6,080,488 A | 6/2000 | Hostettler et al. |
| 6,083,258 A | 7/2000 | Yadav |
| 6,093,463 A | 7/2000 | Thakrar |
| 6,096,070 A | 8/2000 | Ragheb et al. |
| 6,096,525 A | 8/2000 | Patnaik |
| 6,099,562 A | 8/2000 | Ding et al. |
| 6,103,230 A | 8/2000 | Billiar et al. |
| 6,107,416 A | 8/2000 | Patnaik et al. |
| 6,110,188 A | 8/2000 | Narciso, Jr. |
| 6,113,629 A | 9/2000 | Ken |
| 6,117,979 A | 9/2000 | Hendriks et al. |
| 6,120,536 A | 9/2000 | Ding et al. |
| 6,120,904 A | 9/2000 | Hostettler et al. |
| 6,121,027 A | 9/2000 | Clapper et al. |
| 6,125,523 A | 10/2000 | Brown et al. |
| 6,127,173 A | 10/2000 | Eckstein et al. |
| 6,129,761 A | 10/2000 | Hubbell |
| 6,129,928 A | 10/2000 | Sarangapani et al. |
| 6,150,630 A | 11/2000 | Perry et al. |
| 6,153,252 A | 11/2000 | Hossainy et al. |
| 4,776,337 B1 | 12/2000 | Palmaz |
| 6,159,951 A | 12/2000 | Karpeisky et al. |
| 6,160,084 A | 12/2000 | Langer et al. |
| 6,165,212 A | 12/2000 | Dereume et al. |
| 6,166,130 A | 12/2000 | Rhee et al. |
| 6,169,170 B1 | 1/2001 | Gryaznov et al. |
| 6,171,609 B1 | 1/2001 | Kunz |
| 6,174,330 B1 | 1/2001 | Stinson |
| 6,177,523 B1 | 1/2001 | Reich et al. |
| 6,183,505 B1 | 2/2001 | Mohn, Jr. et al. |
| 6,187,045 B1 | 2/2001 | Fehring et al. |
| 6,210,715 B1 | 4/2001 | Starling et al. |
| 6,224,626 B1 | 5/2001 | Steinke |
| 6,228,845 B1 | 5/2001 | Donovan et al. |
| 6,240,616 B1 | 6/2001 | Yan |
| 6,245,076 B1 | 6/2001 | Yan |
| 6,245,103 B1 | 6/2001 | Stinson |
| 6,248,344 B1 | 6/2001 | Ylanen et al. |
| 6,251,135 B1 | 6/2001 | Stinson et al. |
| 6,251,142 B1 | 6/2001 | Bernacca et al. |
| 6,273,913 B1 | 8/2001 | Wright et al. |
| 6,281,262 B1 | 8/2001 | Shikinami |
| 6,284,333 B1 | 9/2001 | Wang et al. |
| 6,287,332 B1 | 9/2001 | Bolz et al. |
| 6,290,721 B1 | 9/2001 | Heath |
| 6,293,966 B1 | 9/2001 | Frantzen |
| 6,303,901 B1 | 10/2001 | Perry et al. |
| 6,312,459 B1 | 11/2001 | Huang et al. |
| 6,327,772 B1 | 12/2001 | Zadno-Azizi et al. |
| 4,733,665 C2 | 1/2002 | Palmaz |
| 6,375,826 B1 | 4/2002 | Wang et al. |
| 6,379,381 B1 | 4/2002 | Hossainy et al. |
| 6,379,648 B1 * | 4/2002 | Day et al. ............ 424/1.29 |
| 6,387,121 B1 | 5/2002 | Alt |
| 6,387,124 B1 | 5/2002 | Buscemi et al. |
| 6,388,043 B1 | 5/2002 | Langer et al. |
| 6,395,326 B1 | 5/2002 | Castro et al. |
| 6,409,761 B1 | 6/2002 | Jang |
| 6,423,092 B2 | 7/2002 | Datta et al. |
| 6,461,632 B1 | 10/2002 | Gogolewski |
| 6,464,720 B2 | 10/2002 | Boatman et al. |
| 6,479,565 B1 | 11/2002 | Stanley |
| 6,485,512 B1 | 11/2002 | Cheng |
| 6,492,615 B1 | 12/2002 | Flanagan |
| 6,494,908 B1 | 12/2002 | Huxel et al. |
| 6,495,156 B2 | 12/2002 | Wenz et al. |
| 6,511,748 B1 | 1/2003 | Barrows |
| 6,517,888 B1 | 2/2003 | Weber |
| 6,527,801 B1 | 3/2003 | Dutta |
| 6,537,589 B1 | 3/2003 | Chae et al. |
| 6,539,607 B1 | 4/2003 | Fehring et al. |
| 6,540,777 B2 | 4/2003 | Stenzel |
| 6,554,854 B1 | 4/2003 | Flanagan |
| 6,565,599 B1 | 5/2003 | Hong et al. |
| 6,569,191 B1 | 5/2003 | Hogan |
| 6,569,193 B1 | 5/2003 | Cox et al. |
| 6,572,672 B2 | 6/2003 | Yadav et al. |
| 6,574,851 B1 | 6/2003 | Mirizzi |
| 6,585,755 B2 | 7/2003 | Jackson et al. |
| 6,592,614 B2 | 7/2003 | Lenker et al. |
| 6,592,617 B2 | 7/2003 | Thompson |
| 6,596,296 B1 | 7/2003 | Nelson et al. |
| 6,613,072 B2 | 9/2003 | Lau et al. |
| 6,626,939 B1 | 9/2003 | Burnside et al. |
| 6,635,269 B1 | 10/2003 | Jennissen |
| 6,645,243 B2 | 11/2003 | Vallana et al. |
| 6,656,162 B2 | 12/2003 | Santini, Jr. et al. |
| 6,664,335 B2 | 12/2003 | Krishnan |
| 6,666,214 B2 | 12/2003 | Canham |
| 6,667,049 B2 | 12/2003 | Janas et al. |
| 6,669,723 B2 | 12/2003 | Killion et al. |
| 6,676,697 B1 | 1/2004 | Richter |
| 6,679,980 B1 | 1/2004 | Andreacchi |
| 6,689,375 B1 | 2/2004 | Wahlig et al. |
| 6,695,920 B1 | 2/2004 | Pacetti et al. |
| 6,706,273 B1 | 3/2004 | Roessler |
| 6,709,379 B1 | 3/2004 | Brandau et al. |
| 6,719,934 B2 | 4/2004 | Stinson |
| 6,719,989 B1 | 4/2004 | Matsushima et al. |
| 6,720,402 B2 | 4/2004 | Langer et al. |
| 6,746,773 B2 | 6/2004 | Llanos et al. |
| 6,752,826 B2 * | 6/2004 | Holloway et al. ............ 623/1.13 |
| 6,753,007 B2 | 6/2004 | Haggard et al. |
| 6,764,505 B1 | 7/2004 | Hossainy et al. |
| 6,808,535 B1 | 10/2004 | Jordan |
| 6,818,063 B1 | 11/2004 | Kerrigan |
| 6,846,323 B2 | 1/2005 | Yip et al. |
| 7,008,642 B1 | 3/2006 | Roorda et al. |
| 2001/0044652 A1 | 11/2001 | Moore |
| 2002/0002399 A1 | 1/2002 | Huxel et al. |
| 2002/0004060 A1 | 1/2002 | Heublein et al. |
| 2002/0004101 A1 | 1/2002 | Ding et al. |
| 2002/0062148 A1 | 5/2002 | Hart |
| 2002/0065553 A1 | 5/2002 | Weber |
| 2002/0111590 A1 | 8/2002 | Davila et al. |
| 2002/0116050 A1 | 8/2002 | Kocur |
| 2002/0138133 A1 | 9/2002 | Lenz et al. |
| 2002/0161114 A1 | 10/2002 | Gunatillake et al. |
| 2003/0033001 A1 | 2/2003 | Igaki |
| 2003/0093107 A1 | 5/2003 | Parsonage et al. |
| 2003/0099682 A1 * | 5/2003 | Moussy et al. ............ 424/423 |
| 2003/0100865 A1 | 5/2003 | Santini, Jr. et al. |
| 2003/0105518 A1 | 6/2003 | Dutta |
| 2003/0105530 A1 | 6/2003 | Pirhonen |
| 2003/0147966 A1 * | 8/2003 | Franzen et al. ............ 424/491 |
| 2003/0171053 A1 | 9/2003 | Sanders |
| 2003/0187495 A1 | 10/2003 | Cully et al. |
| 2003/0208259 A1 | 11/2003 | Penhasi |
| 2003/0209835 A1 | 11/2003 | Chun et al. |
| 2003/0226833 A1 | 12/2003 | Shapovalov et al. |
| 2003/0236563 A1 | 12/2003 | Fifer |
| 2004/0024419 A1 * | 2/2004 | Slepian et al. ............ 606/214 |
| 2004/0052858 A1 | 3/2004 | Wu et al. |
| 2004/0093077 A1 | 5/2004 | White et al. |
| 2004/0098095 A1 | 5/2004 | Burnside et al. |
| 2004/0111149 A1 | 6/2004 | Stinson |

(56) References Cited

U.S. PATENT DOCUMENTS

| | | | |
|---|---|---|---|
| 2004/0127970 A1 | 7/2004 | Saunders et al. | |
| 2004/0143317 A1 | 7/2004 | Stinson et al. | |
| 2004/0167610 A1 | 8/2004 | Fleming, III | |
| 2004/0193255 A1 | 9/2004 | Shanley et al. | |
| 2005/0119723 A1 | 6/2005 | Peacock | |
| 2005/0142202 A1 | 6/2005 | Roorda et al. | |
| 2005/0181015 A1 | 8/2005 | Zhong | |
| 2005/0209680 A1 | 9/2005 | Gale et al. | |
| 2005/0267565 A1* | 12/2005 | Dave et al. | 623/1.15 |
| 2006/0002978 A1* | 1/2006 | Shea et al. | 424/426 |
| 2006/0018948 A1 | 1/2006 | Guire et al. | |
| 2007/0020320 A1* | 1/2007 | David et al. | 424/445 |
| 2007/0141100 A1* | 6/2007 | Sung et al. | 424/423 |
| 2007/0141163 A1* | 6/2007 | Vitaliano et al. | 424/490 |

FOREIGN PATENT DOCUMENTS

| | | |
|---|---|---|
| DE | 198 56 983 | 12/1999 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0 970 711 | 1/2000 |
| GB | 2 247 696 | 3/1992 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/29647 | 11/1995 |
| WO | WO 98/04415 | 2/1998 |
| WO | WO 99/03515 | 1/1999 |
| WO | WO 99/16386 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 01/95834 | 12/2001 |
| WO | WO 2004/023985 | 3/2004 |
| WO | WO 2004/110302 | 12/2004 |
| WO | WO 2005/115496 | 12/2005 |

OTHER PUBLICATIONS

Lavasanifar et al. Poly(ethylene oxide)-block-poly(L-amino acid) micelles for drug delivery. Advanced Drug Delivery Reviews 54 (2002) 169-190.*

U.S. Appl. No. 10/317,435, Hossainy et al., filed Dec. 11, 2002.

Anonymous, *Bioabsorbable stent mounted on a catheter having optical coherence tomography capabilities*, Research Disclosure, Sep. 2004, pp. 1159-1162.

Ansari, *End-to-end tubal anastomosis using an absorbable stent*, Fertility and Sterility, vol. 32(2), pp. 197-201 (Aug. 1979).

Ansari, *Tubal Reanastomosis Using Absorbable Stent*, International Journal of Fertility, vol. 23, No. 4, pp. 242-243 (1978).

Bull, *Parylene Coating for Medical Applications*, Medical Product Manufacturing News 18,1 pg. (Mar. 1993).

Casper et al., *Fiber-Reinforced Absorbable Composite for Orthopedic Surgery*, Polymeric Materials Science and Engineering, 53: pp. 497-501 (1985).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).

Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).

Devanathan et al., *Polymeric Conformal Coatings for Implantable Electronic Devices*, IEEE Transactions on Biomedical Engineering, vol. BME-27(11), pp. 671-675 (1980).

Elbert et al., *Conjugate Addition Reactions Combined with Free-Radical Cross-Linking for the Design of Materials for Tissue Engineering*, Biomacromolecules 2, pp. 430-441 (2001).

Hahn et al., *Biocompatibility of Glow-Discharge-Polymerized Films and Vacuum-Deposited Parylene*, J Applied Polymer Sci, 38, pp. 55-64 (1984).

Hahn et al., *Glow Discharge Polymers as Coatings for Implanted Devices*, ISA, pp. 109-111 (1981).

He et al., *Assessment of Tissue Blood Flow Following Small Artery Welding with an Intraluminal Dissolvable Stent*, Microsurgery, vol. 19(3), pp. 148-152 (1999).

Kelley et al., *Totally Resorbable High-Strength Composite Material*, Advances in Biomedical Polymers, 35, pp. 75-85 (1987).

Kubies et al., *Microdomain Structure in polylactide-block-poly(ethylene oxide) copolymer films*, Biomaterials 21, pp. 529-536 (2000).

Kutryk et al., *Coronary Stenting: Current Perspectives*, a companion to the Handbook of Coronary Stents pp. 1-16 (1999).

Martin et al., *Enhancing the biological activity of immobilized osteopontin using a type-1 collagen affinity coating*, J. Biomed. Mater Res 70A, pp. 10-19 (2004).

Mauduit et al., *Hydrolytic degradation of films prepared from blends of high and low molecular weight poly(DL-lactic acid)s*, J. Biomed. Mater. Res. v. 30, pp. 201-207 (1996).

Middleton et al., *Synthetic biodegradable polymers as orthopedic devices*, Biomaterials, vol. 21, pp. 2335-2346 (2000).

Muller et al., *Advances in Coronary Angioplasty: Endovascular Stents*, Coron. Arter. Dis., 1(4), pp. 438-448 (Jul./Aug. 1990).

Nichols et al., *Electrical Insulation of Implantable Devices by Composite Polymer Coatings*, ISA Transactions, 26(4), pp. 15-18 (1987).

Peuster et al., *A novel approach to temporary stenting: degradable cardiovascular stents produced from corrodible metal-results 6-18 months after implantation into New Zealand white rabbits*, Heart 86, pp. 563-569 (2001).

Pietrzak et al., *Bioabsorbable Fixation Devices: Status for the Craniomaxillofacial Surgeon*, J. Craniofaxial Surg. 2, pp. 92-96 (1997).

Pietrzak et al., *Bioresorbable implants—practical considerations*, Bone v. 19, No. 1, Supplement Jul. 1996: 109S-119S.

Redman, *Clinical Experience with Vasovasostomy Utilizing Absorbable Intravasal Stent*, Urology, vol. 20(1), pp. 59-61 (Jul. 1982).

Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).

Schatz, *A View of Vascular Stents*, Circulation, 79(2), pp. 445-457 (Feb. 1989).

Schmidt et al., *Long-Term Implants of Parylene-C Coated Microelectrodes*, Med & Biol Eng & Comp, 26(1), pp. 96-101 (Jan. 1988).

Spagnuolo et al., *Gas 1 is induced by VE-cadherin and vascular endothelial growth factor and inhibits endothelial cell apoptosis*, Blood 103, pp. 3005-3012 (2004).

Tamai et al., *Initial and 6-Month Results of Biodegradable Poly-I-Lactic Acid Coronary Stents in Humans*, Circulation, pp. 399-404 (Jul. 25, 2000).

(56) References Cited

OTHER PUBLICATIONS

Tsuji et al., *Biodegradable Polymeric Stents*, Current Interventional Cardiology Reports 3, pp. 10-17 (2001).
Völkel et al., *Targeting of immunoliposomes to endothelial cells using a single-chain Fv fragment directed against human endoglin (CD105)*, Biochimica et Biophysica Acta 1663, pp. 158-166 (2004).
von Recum et al., *Degradation of polydispersed poly(L-lactic acid) to modulate lactic acid release*, Biomaterials 16, pp. 441-445 (1995).
Yau et al., Modern Size-Exclusion Liquid Chromatography, Wiley-Interscience Publication, IX-XV (1979).
International Search Report for PCT/US2006/031737 filed Aug. 14, 2006, mailed Jan. 3, 2007, 14 pgs.
International Search Report for PCT/US2006/048051, mailed Oct. 7, 2008, 14 pgs.
Laser Focus World (online), Rapid prototyping evolves into custom manufacturing, Retrieved (Dec. 18, 2000), from www.laserfocusworld.com/display_article/227426/12/none/none/Feat/Rapid-prototyping-evolves-into-custom-manufacturing.
Kay et al., Cardiac Catheterization and Percutaneous Interventions, 2004, Taylor&Francis, p. 243.

\* cited by examiner

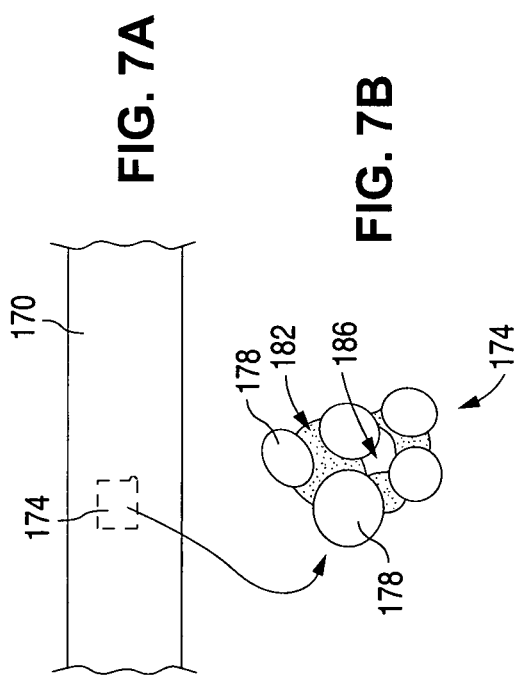
FIG. 7A
FIG. 7B
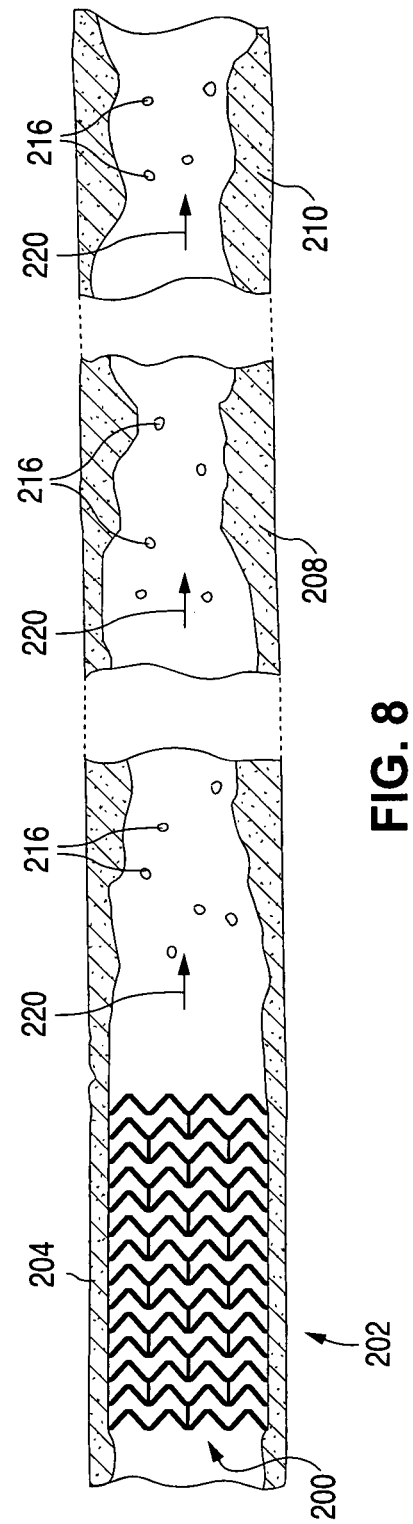
FIG. 8

CONTROLLED DISINTEGRATING IMPLANTABLE MEDICAL DEVICES

BACKGROUND OF THE INVENTION

1. Field of the Invention

This invention relates to implantable medical devices for treating bodily disorders local and distal to a region of implantation.

2. Description of the State of the Art

This invention relates generally to implantable medical devices for treating bodily disorders. A typical treatment regimen with an implantable medical device involves implantation of a device at a selected treatment location. During treatment it may be necessary for the device to support body tissue. Therefore, the structure of a device may include load bearing structural elements or substrate to hold the device in place and to resist forces imposed by surrounding tissue.

The treatment of a bodily disorder may also involve local delivery of a bioactive agent or drug to treat a bodily disorder. The agent may be incorporated into the device in a variety of ways and delivered directly to an afflicted region at or adjacent to a region of implantation.

Additionally, in many treatment situations, the presence of the device is required only for a limited period of time. Therefore, a device may be composed in whole or in part of materials that degrade, erode, or disintegrate through exposure to conditions within the body until the treatment regimen is completed.

An example of such devices includes radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

The stent must be capable of withstanding the structural loads, namely radial compressive forces, imposed on the stent as it supports the walls of a vessel. Therefore, a stent must possess adequate radial strength, which is the ability of a stent to resist radial compressive forces. Once expanded, the stent must adequately maintain its size and shape throughout its service life despite the various forces that may come to bear on it, including the cyclic loading induced by the beating heart. In addition, the stent must possess sufficient flexibility to allow for crimping, expansion, and cyclic loading.

The structure of a stent is typically composed of scaffolding or substrate that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment).

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers can be configured to completely erode after the clinical need for them has ended.

In some treatment situations, local treatment of bodily tissue disorders with an implantable medical device may be difficult or impossible. This inability may be due to the fact that tissue disorders may be diffuse and in multiple locations. Local treatment in such situations may require a multiplicity of devices. For example, vascular disorders can include lesions in multiple locations, such as diffuse lesions along vessels, multi-vessel lesions, and bifurcated vessel lesions. In addition, local treatment may be impossible because an afflicted region of tissue may be inaccessible to implantation of a device. For example, a diseased vessel may be too small for implantation of a stent.

Thus, it would be desirable to have an implantable medical device that can be used to treat tissue disorders both local and distal to the location of implantation. Additionally, it may also be desirable for such devices to be capable of disintegrating once a treatment regimen is completed.

SUMMARY OF THE INVENTION

Certain embodiments of the present invention include an implantable medical device that may include a body structure with at least a portion of the body structure including a plurality of particles releasably bound together by an erodible binder. The particles may be configured to be released from the body structure of the device due to erosion of the body structure during use of the device. The released particles may be adapted to treat a bodily disorder.

Certain embodiments of the present invention include a method of treating a bodily disorder using an implantable medical device that may include disposing an implantable medical device at an implantation bodily region. At least a portion of a body structure of the device may include a plurality of particles releasably bound together by an erodible binder. The particles being may be adapted to be released from the body structure of the device due to erosion of the body structure. The particles may be adapted to treat a bodily disorder. The method may further include allowing at least some of the particles to be released from the body structure of the device.

Certain embodiments of the present invention include a method of treating a bodily disorder using an implantable medical device that may include disposing an implantable medical device at an implantation bodily region. At least a portion of a body structure of the device may include a plurality of particles releasably bound together by an erodible binder. The particles may be adapted to be released from the body structure of the device due to erosion of the body structure. The method may further include allowing an active agent within the particles to treat a bodily disorder at or near the implantation region.

Certain embodiments of the present invention include a method of fabricating an implantable medical device that may include applying a fluid on a predefined portion of a plurality of particles. The method may further include allowing the fluid to releasably bind together the predefined portion of particles with a binder to form a layer including the particles bound together with the binder. The particles may be configured to be released from the device due to erosion of the device during use. The released particles may be adapted to treat a bodily disorder with an active agent in the particles.

BRIEF DESCRIPTION OF THE DRAWINGS

FIG. 7A depicts a two-dimensional view of a side-wall of a segment of a strut.

FIG. 7B depicts a close-up view of a portion of the strut segment in FIG. 7A.

FIG. 8 depicts a stent implanted in a vascular segment with a diseased site.

DETAILED DESCRIPTION OF THE INVENTION

Figure 1:
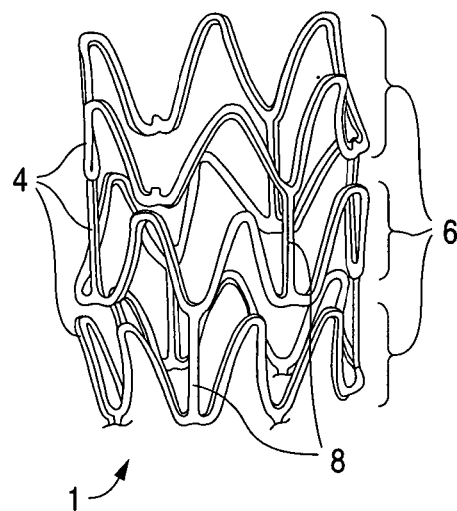
FIG. 1 depicts a three-dimensional view of a stent.

In general, treatment of a bodily disorder with an implantable medical device, such as a stent, may require the device to perform several functions. In some cases, a device must be able to provide structural support to the body tissue in which it is implanted. Therefore, a device can have virtually any structural pattern that is compatible with body tissue in which it is implanted. In addition, a device may also deliver a bioactive agent to an implanted region for treatment of a bodily disorder. Furthermore, it may be desirable for the device to disintegrate and disappear from the implanted region once treatment is completed.

Various embodiments of the present invention relate to implantable medical devices for treating bodily tissue disorders local and distal to a region of implantation of the device. In some embodiments, the device may be configured to disintegrate and disappear from the region of implantation once treatment is completed. The device may disintegrate by one or more mechanisms, including dissolution, chemical breakdown, and rheological forces.

The term "implantable medical devices" includes, but is not limited to, self-expandable stents, balloon-expandable stents, stent-grafts, grafts (e.g., vascular grafts such as aortic grafts), artificial heart valves, cerebrospinal fluid shunts, pacemaker electrodes, and endocardial leads (e.g., FINE-LINE and ENDOTAK, available from Guidant Corporation, Santa Clara, Calif.). The underlying structure of the device can be of virtually any design. Implantable medical devices may also include urethral stents, pulmonary stents, implants for the gastro-intestinal tract, anastomotic couplers, and implantable catheter ports (e.g., for dialysis treatment).

For the purposes of the present invention, the following terms and definitions apply:

"Bodily disorder" refers to any condition that adversely affects the function of the body.

"Solvent" is defined as a substance capable of dissolving or dispersing one or more other substances or capable of at least partially dissolving or dispersing the substance(s) to form a uniformly dispersed mixture at the molecular- or ionic-size level. The solvent of a polymer should be capable of dissolving at least 0.1 mg of the polymer in 1 ml of the solvent, and more narrowly 0.5 mg in 1 ml at ambient temperature and ambient pressure. The "strength" of a solvent refers to the degree to which a solvent may dissolve a polymer. The stronger a solvent is, the more polymer the solvent can dissolve.

"Dissolve" refers to a substance passing into solution on a molecular scale with or without chemical breakdown of the solid.

The term "treatment" includes prevention, reduction, delay, stabilization, or elimination of a bodily tissue disorder, such as a vascular disorder. In some embodiments, treatment also includes repairing damage caused by the disorder and/or mechanical intervention.

"Use" includes delivery of a device to a treatment site and deployment or implantation of the device at a treatment site.

A "bioactive" or "active" agent can be any substance capable of exerting an effect including, but not limited to, therapeutic, prophylactic, or diagnostic. Bioactive agents may include anti-inflammatories and antiproliferatives and other bioactive agents.

"Sintering" is a process of fabrication where particles are bonded together without entirely melting the particles. Particles may be pressed together or molded into a desired shape. A considerable amount of pressure is first applied to press the particles together. Then, the particles are heated to temperatures slightly below the melting point of the particle material. Without entirely melting, the particles bond to each other at their respective surfaces. A porous structure may be formed since spaces may remain between the bonded particles.

In general, the structure of an implantable device includes structural elements, scaffolding, or a substrate that may be the primary source of structural support. For example, a stent typically is composed of a pattern or network of circumferential rings and longitudinally extending interconnecting structural elements of struts or bar arms. In general, the struts are arranged in patterns, which are designed to contact the lumen walls of a vessel and to maintain vascular patency. A myriad of strut patterns are known in the art for achieving particular design goals.

FIG. 1 depicts a three-dimensional view of a stent 1 which is made up of struts 4. Stent 1 has interconnected cylindrical rings 6 connected by linking struts or links 8. The embodiments disclosed herein are not limited to stents or to the stent pattern illustrated in FIG. 1. The embodiments are easily applicable to other stent patterns and other devices. The variations in the structure of patterns are virtually unlimited.

Conventionally, a stent such as stent 1 may be fabricated from a tube by forming a pattern with a technique such as laser cutting. Representative examples of lasers that may be used include an excimer, carbon dioxide, and YAG. In other embodiments, chemical etching may be used to form a pattern on the elongated tube.

In some embodiments, the diameter of the stent may be between about 0.2 mm and about 5.0 mm, or more narrowly between about 1 mm and about 3 mm. Unless otherwise specified, the "diameter" of the tube refers to the outside diameter of tube.

Furthermore, bodily tissue disorders may be treated with active agent systemically or locally. Systemic treatment refers to administering an active agent to the body in a manner that tends to expose the body as a whole or a substantial portion of the body to the active agent. For example, systemic treatment may involve administration of an active agent by injection, intraveneously, orally, etc. Local treatment refers to administration of an active agent at or adjacent to the bodily tissue disorder. For example, implantable medical devices may provide for the local administration or delivery of an active agent at a diseased site at or adjacent to the region of implantation. Stents, for example, are used not only for mechanical intervention, but also as vehicles for providing biological therapy.

A medicated device, such as a stent, may be fabricated by coating the surface of either a metallic and/or polymeric scaffolding to produce a drug reservoir layer on the surface. The drug reservoir layer typically includes a polymeric carrier that includes an active agent or drug. To fabricate a conventional coating, a polymer, or a blend of polymers, can be applied on the device using commonly used techniques known to those having ordinary skill in the art. A composition for application to a device may include a solvent, a polymer dissolved in the solvent, and an active agent dispersed in the blend. The composition may be applied to the device, for example, by immersing the device in the composition or by spraying the composition onto the device. The solvent is allowed to evaporate, leaving on the device substrate surfaces a coating of the polymer and the active agent impregnated in the polymer.

In some embodiments, scaffolding or substrate may also serve as a carrier of an active agent or drug. For example, an active agent may be mixed or dispersed within at least a portion of polymeric scaffolding.

In order to provide an efficacious concentration to a diseased site, systemic administration of an active agent often produces adverse or even toxic side effects for the patient. Local delivery may be a preferred method of treatment in that smaller total levels of medication are administered in comparison to systemic dosages since the doses are concentrated at a specific site. Local delivery can produce fewer side effects and achieve more favorable results.

Figure 2:
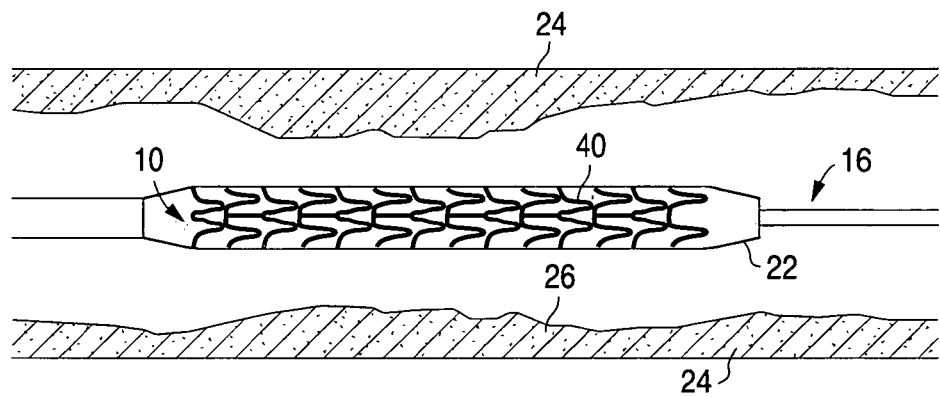
FIG. 2 depicts a stent mounted on a catheter within a vascular segment.
Figure 3:
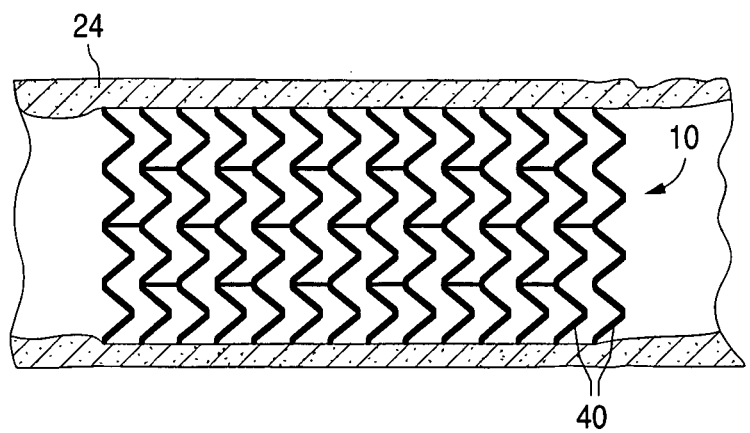
FIG. 3 depicts a stent implanted in a vascular segment.

FIGS. 2-3 illustrate local treatment of diseased sites in a bodily lumen with a stent. FIGS. 2-3 can represent any balloon expandable stent 10 with which various configurations can be used. The explanation below can easily be adapted to a self-expandable stent. FIG. 2 depicts a stent 10 with interconnected cylindrical rings 40 mounted on a catheter assembly 16 which is used to deliver stent 10 and implant it in a bodily lumen.

For example, a bodily lumen may include a coronary artery, peripheral artery, or other vessel or lumen within the body. The catheter assembly is configured to advance through the patient's vascular system by advancing over a guide wire by any of the well-known methods known in the art. The stent is mounted on expandable member 22 (e.g., a balloon) and is crimped tightly thereon, so that the stent and expandable member present a low profile diameter for delivery through the arteries.

As shown in FIG. 2, a partial cross-section of an artery 24 has a diseased area or lesion 26. The diseased area may be a small amount of plaque that has been previously treated by angioplasty or other repair procedure. Stent 10 is used to repair a diseased or damaged arterial wall as shown in FIG. 2, or a dissection, or a flap, all of which are commonly found in the coronary arteries and other vessels. Stent 10 and other embodiments of stents can also be placed and implanted without any prior angioplasty.

In a typical procedure to implant stent 10, catheter assembly 16 is advanced through the patient's vascular system by well-known methods to the diseased area 26. The expandable member or balloon 22 is inflated by well-known means so that it expands radially outwardly and in turn expands the stent radially outwardly until the stent is apposed to the vessel wall. The expandable member is then deflated and the catheter withdrawn from the patient's vascular system. In FIG. 3, the implanted stent remains in the vessel after the balloon has been deflated and the catheter assembly and guide wire have been withdrawn from the patient.

Stent 10 holds open the artery after the catheter is withdrawn, as illustrated by FIG. 3. As indicated above, a stent may be formed from a cylindrical tube with a constant wall thickness. Thus, the straight and undulating or curved components of the stent are relatively flat in transverse cross-section. Thus, when the stent is expanded, a flat abluminal surface may be pressed into the wall of the artery. As a result, the stent may not interfere with the blood flow through the artery. After the stent is pressed into the wall of the artery, it may become covered with endothelial cell growth which further minimizes blood flow interference. The undulating or curved portion of the stent provides good tacking characteristics to prevent stent movement within the artery. Because cylindrical rings 40 are closely spaced at regular intervals, they provide uniform or relatively uniform support for the wall of the artery. Consequently the rings are well adapted to tack up and hold in place small flaps or dissections in the wall of the artery.

As discussed above, some treatments with implantable medical devices require the presence of the device only for a limited period of time. Once treatment is complete, which may include structural tissue support and/or drug delivery, it may be desirable for the stent to be removed or disappear from the treatment location. One way of having a device disappear may be by fabricating the device in whole or in part from materials that erode or disintegrate through exposure to conditions within the body. Thus, erodible portions of the device can disappear or substantially disappear from the implant region after the treatment regimen is completed. After the process of disintegration has been completed, no portion of the device, or an erodible portion of the device will remain. In some embodiments, very negligible traces or residue may be left behind.

The terms degrade, absorb, and erode, as well as degraded, eroded, and absorbed, are used interchangeably and refer to materials that are capable of being completely eroded, or absorbed when exposed to bodily conditions. Such materials may be capable of being gradually resorbed, absorbed, and/or eliminated by the body. A device made of such materials may disintegrate from a region of implantation.

The duration of a treatment period depends on the bodily disorder that is being treated. In treatments of coronary heart disease involving use of stents in diseased vessels, the duration can be in a range from about a month to a few years. However, the duration is typically in a range from about six to twelve months.

Several mechanisms may be relied upon for erosion and disintegration of implantable devices which include, but are not limited to, mechanical, chemical breakdown, dissolution, and breakdown due to rheological forces. Therefore, bodily conditions can include, but are not limited to, all conditions associated with bodily fluids (contact with fluids, flow of fluids) and mechanical forces arising from body tissue in direct and indirect contact with a device. The current technology of vascular and other types of devices tend to rely principally on chemical breakdown involving enzymatic and/or hydrolytic cleavage of device material due to exposure to bodily fluids such as blood.

In general, polymers can be biostable, bioabsorbable, biodegradable, or bioerodable. Biostable refers to polymers that are not biodegradable. The terms biodegradable, bioabsorbable, and bioerodable, as well as degraded, eroded, and absorbed, are used interchangeably and refer to polymers that are capable of being completely eroded or absorbed after implantation, e.g., when exposed to bodily fluids such as blood and can be gradually resorbed, absorbed, and/or eliminated by the body.

Chemical breakdown of biodegradable polymers results in changes of physical and chemical properties of the polymer, for example, following exposure to bodily fluids in a vascular environment. The changes in properties may include a decrease in molecular weight, deterioration of mechanical properties, and decrease in mass due to erosion or absorption. Mechanical properties may correspond to strength and modulus of the polymer. Deterioration of the mechanical properties of the polymer decreases the ability of a device, for example, to provide mechanical support in a vessel. The decrease in molecular weight may be caused by, for example, hydrolysis and/or metabolic processes. Hydrolysis is a chemical process in which a molecule is cleaved into two parts by the addition of a molecule of water. Consequently, the degree of degradation in the bulk of a polymer is strongly dependent on the diffusivity, and hence the diffusion rate of water in the polymer.

Several characteristics or parameters of the degradation process are important in designing biodegradable devices. These include an average erosion rate of a device, the erosion profile, the half-life of the degrading polymer, and mechanical stability of a device during the degradation process. The "average erosion rate" may be an average erosion rate over any selected time interval:

$$\text{Average erosion rate} = (m_2 - m_1)/(t_2 - t_1)$$

where "m" refers to mass of the device, "t" refers to a time during erosion, and $m_1$ and $m_2$ are the masses of the device at $t_1$ and $t_2$ during erosion. For instance, the selected time interval may be between the onset of degradation and another selected time. Other selected times, for example, may be the time for about 25%, 50%, 75%, or 100% (complete erosion) of the device to erode. Complete erosion may correspond approximately to the time required for treatment by the device. As an example of the time frame of erosion, a biodegradable polymeric stent may be completely eroded in about six to eighteen months.

The "half-life" of a degrading polymer refers to the length of time for the molecular weight of the polymer to fall to one half of its original value. See e.g., J. C. Middleton and A. J. Tipton, Biomaterials, Vol. 21 (23) (2000) pp. 2335-2346.

In addition, metals may be considered to be biostable or bioerodible. Some metals are considered bioerodible since they tend to erode or corrode relatively rapidly when implanted or when exposed to bodily fluids. Biostable metals refer to metals that are not bioerodible. Biostable metals have negligible erosion or corrosion rates when implanted or when exposed to bodily fluids.

In general, metal erosion or corrosion involves a chemical reaction between a metal surface and its environment. Erosion or corrosion in a wet environment, such as a vascular environment, results in removal of metal atoms from the metal surface. The metal atoms at the surface lose electrons and become actively charged ions that leave the metal to form salts in solution.

Representative examples of biodegradable metals that may be used to fabricate an implantable medical device may include, but are not limited to, magnesium, zinc, and iron. As an example, of the time frame of erosion, an erodible metallic stent may be completely eroded between about a week and about three months, or more narrowly, between about one month and about two months.

Local treatment of some regions having bodily tissue disorders may be difficult or impossible for several reasons. Body tissue may include multiple afflicted locations requiring multiple implanted devices. An afflicted region may also be inaccessible to implantation. Such regions may be treated systemically. However, as pointed out above, systemic delivery has disadvantages.

Figure 4:
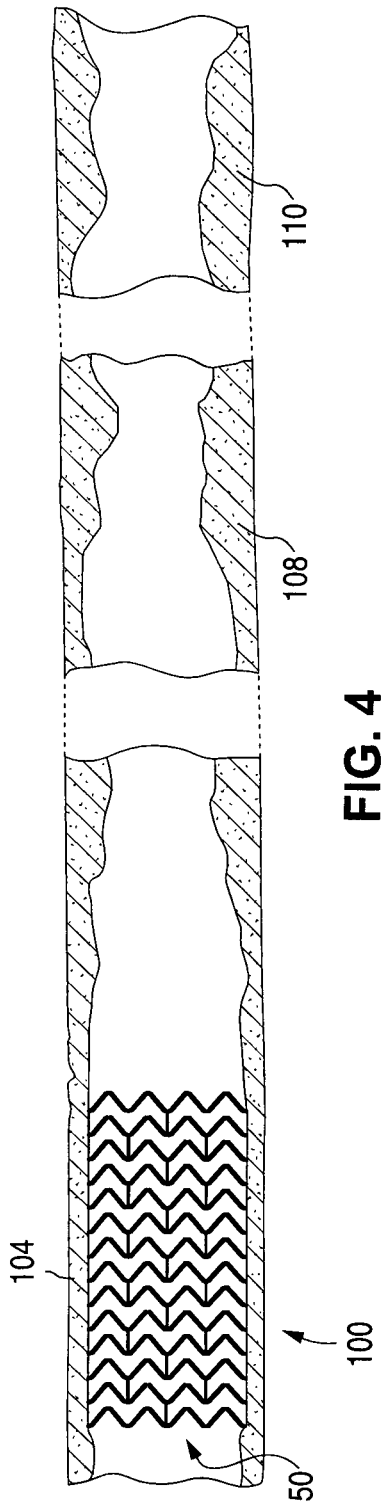
FIGS. 4-6 depict vascular segments with diseased sites.
Figure 6:
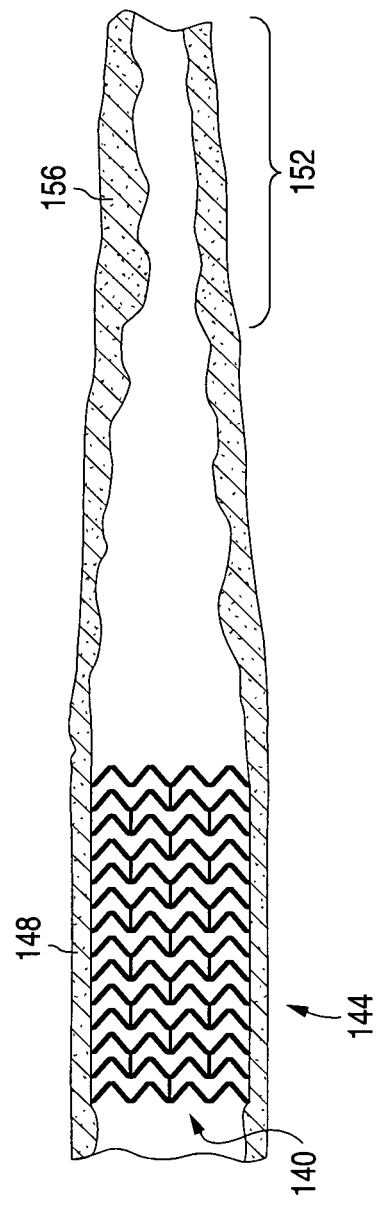
Figure 5:
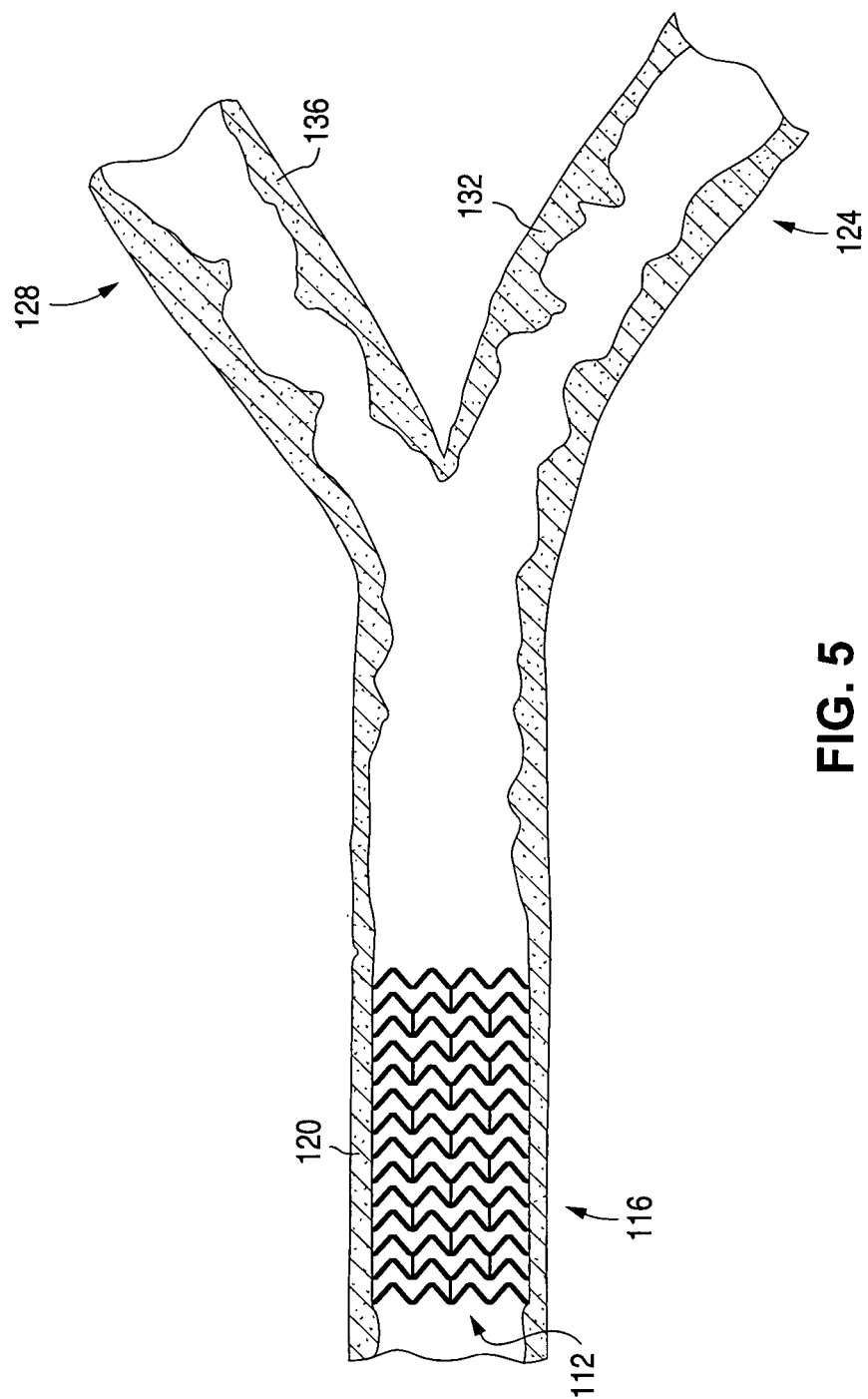

As an illustration, FIGS. 4-6 depict examples of vascular disorders that are difficult to treat locally with a stent. FIG. 4 depicts a stent 90 implanted in a vascular segment 100 at a diseased site or lesion 104. Stent 10 provides mechanical support and delivers active agents to treat lesion 104. Vascular segment 100 also includes multiple lesions diffusely distributed in relation to lesion 104, such as lesions 108 and 110. Local treatment of lesions 108 and 110 would require implantation of additional stents at their respective locations.

FIG. 5 depicts a stent 112 implanted in a vascular segment 116 at a lesion 120. At a location distal to lesion 120, vascular segment 116 bifurcates into vascular segments 124 and 128. Vascular segments 124 and 128 have lesions 132 and 136. Local treatment of lesions 132 and 136 would require implantation of additional stents at their respective locations.

FIG. 6 depicts a stent 140 implanted in vascular segment 144 at lesion 148. Vascular segment 144 narrows distally further down from lesion 148. A portion 152 of segment 144 has a lesion 156. However, portion 152 is too narrow for implantation of a stent. Treatment of a bodily lumen with a stent is typically limited to a lumen diameter greater than about 1 micron.

As indicated above, embodiments of the present invention relate to implantable medical devices for treating bodily tissue disorders local and distal to a region of implantation of the device. The devices described herein allow treatment of afflicted regions distal to the site of implantation of a device without the problems associated with systemic treatment, but with the advantages of local treatment.

In certain embodiments, an implantable medical device may include a body structure with at least a portion of the body structure including a plurality of particles releasably bound together by an erodible binder. The particles may be configured to be released from the body structure of the device due to erosion of the body structure during use of the device. In some embodiments, the particles may be adapted to treat a bodily disorder. For example, at least some of the particles may include an active agent for treatment of the disorder.

FIG. 7 illustrates an example of a strut from a stent including particles bound together with a binder according to an embodiment described above. FIG. 7A depicts a two-dimensional view of a sidewall of a segment of a strut 170. FIG. 7B shows a close-up view of a portion 174 of strut 170. Portion 174 has particles 178 bound together by binder 182. The structure of strut 170 may also include cavities or pores 186.

In one embodiment, at least some of the released particles may be adapted to be transported to a selected bodily region distal from a local region of implantation. The particles may deliver an active agent included in the particle to the distal region for treatment of a disorder at or adjacent to the region. The active agent may elute from the particles to treat the disorder.

Thus, certain embodiments of a method of treating a diseased region within a body may include disposing the implantable medical device at or within an implantation bodily region. The method may further include allowing at least some of the particles to be released from the body structure of the device. In some embodiments, the released particles may be transported to a bodily region distal from the implantation bodily region to treat a bodily disorder at the distal region. For example, the device may be a stent implanted at or near the site of a vascular region with a lesion. After being released from the device, the particles may be transported to a distal or per-adventitial vasculature region having a lesion. An active agent eluting from the particles may treat the afflicted distal vascular region.

In some embodiments, an active agent within the particles may treat a bodily disorder at or near the implantation region. The active agent may diffuse from bound and/or released particles into bodily tissue at or near the implantation region to treat the bodily disorder. The bodily tissue may include outer vessel wall layers such as per adventitia.

As an example, FIG. 8 depicts a stent 200 implanted in a vascular segment 202 for treating lesion 204. Vascular segment 202 has diseased distal regions 208 and 210. Stent 200 is adapted to release particles bound together with a binder. Released particles 216 (not necessarily to scale) are transported in the direction of blood flow as shown by arrows 220. Released particles 216 are adapted to treat distal regions 208 and 210 with an active agent within the particles.

In one embodiment, one or more of the plurality of particles may include more than one type of active agent. Alternatively, more than one type of particle may be released, where different types may include different agents. Each type of active agent may be adapted to treat a selected bodily disorder. For example, a particle for release from a stent may include an antiproliferative drug and an anti-inflammatory drug. The anti-inflammatory drug may be treat inflammation locally prior to release and the antiproliferative drug may be used to treat distal regions after release of the particle. In addition, a particle may include different types of active agents to treat different disorders in distal regions.

In addition, particles may be biostable or bioerodible. It is generally desirable for erodible particles to have a slower degradation rate than binder material. Additionally, a particle material should be selected so that the particles do not undergo substantial erosion prior to release and prior to treatment of a distal region.

In certain embodiments, the particles may include nanoparticles and/or microparticles. A nanoparticle refers to a particle with a characteristic length (e.g., diameter) in the range of about 1 nm to about 1,000 nm. A microparticle refers to a particle with a characteristic length in the range of greater than 1,000 nm and less than about 10 micrometers.

Embodiments of the device can include numerous types and configurations of particles. Representative examples of materials that may be used for particles include, but are not limited to, a biostable polymer; a bioabsorbable polymer; a biosoluble material; a biopolymer; a biostable metal; a bio-erodible metal; a block copolymer of a bioabsorbable polymer or a biopolymer; a ceramic material such as a bioabsorbable glass; salts; fullerenes; lipids; carbon nanotubes; or a combination thereof. Particles may also include micelles or vesicles.

Particles may have bioactive agents mixed, dispersed, or dissolved in the particle material. Particles may also be coated with an active agent. In other embodiments, particles can also have an outer shell of polymer, metal, or ceramic with inner compartment containing an active agent. In an embodiment, particles may include bioresorbable glass with bioactive agent encapsulating or embedded within the particle. In some embodiments, particles may be designed to use a combination of the above, e.g., a particle may include a polymeric drug, or a drug impregnated core coated with a bioerodible metal. In addition, particles may include fullerenes coated with a bioactive agent.

As indicated, in some embodiments, particles may include micelles. The micelles may be loaded with active agent formed from block copolymers and/or lipids. A "micelle" refers to an aggregate (or cluster) of surfactant molecules. Micelles tend to form when the concentration of surfactant is greater than the critical micelle concentration. "Surfactants" refer to chemicals that are amphipathic, which means that they contain both hydrophobic and hydrophilic groups. Micelles can exist in different shapes, including spherical, cylindrical, and discoidal. Micelles may be stabilized by crosslinking of the surfactant molecules that form the micelle.

Additionally, particles may be vesicles loaded with bioactive formed from block copolymers and or lipids. A vesicle is a relatively small and enclosed compartment or shell formed by at least one lipid bilayer. The vesicle may also be stabilized by crosslinking the lipid bilayer shell.

In some embodiments, the binder that holds the particles to the body structure of the device may be composed in whole or in part of a bioerodible material. The binder may begin to erode upon exposure to bodily conditions. In addition, the particles may also be composed in whole or in part of an erodible material. The release of the particles may due to erosion of the binder and/or particles.

Representative examples of materials that may be used for a binder include, but are not limited to, a bioabsorbable polymer; a biostable, but biosoluble polymer; a biosoluble material; a biopolymer; a biostable metal; a bioerodible metal; a block copolymer of a bioabsorbable polymer or a biopolymer; salts; bioerodible glass; or a combination thereof.

As described above, the mechanism of erosion and release of the particles may be due to one or more mechanisms. In one embodiment, erosion may be due to chemical breakdown of the binder material. In some embodiments, at least some of the particles can include erodible material. Erosion may also be due to dissolution of the binder material and/or particles. It may be advantageous for the particles to have a slower erosion rate than the binder material.

In other embodiments, rheological forces may facilitate erosion of the body structure and release of the particles. For example, the force of fluids flowing through a bodily lumen may cause detachment of particles. The attachment of such particles may have been weakened by erosion of binder material that binds the particles to the body structure of the device. Rheological forces may arise from the flow of blood and other fluids in bodily lumen.

In one embodiment, the binder may include an active agent. The binder may deliver the active agent for local treatment of a bodily disorder at the location of implantation of the device. In one embodiment, the binder may have active agent (s) for treating disorder(s) locally and the particles may have active agent(s) for treating the same and/or different disorders distally.

In other embodiments, the plurality of particles may include particles having the same or substantially the same treatment properties. Treatment properties may include, but are not limited to, type(s) of active agent included in each particle, release rate of active agents from the particle, degradation rate, and size. In other embodiments, the plurality of particles may have particles with different treatment properties. Some particles may have different types of active agents, different release rates than other particles, different degradation rates, and different sizes.

In some embodiments, the plurality of particles may be arranged such that selected particles of the plurality of particles are released during a selected time or are released according to a sequence as compared to other particles. In one embodiment, the particles may be selected based on treatment properties of the particles. For example, it may be desirable to treat particular disorders before others in regions distal to the implant location of the device. Therefore, particles having active agents for treating such disorders may be configured to be released prior to other particles that have other types of active agents. Such particles may be located closer to a surface of the device where they may be released sooner.

In additional embodiments, at least some of the particles and binder may be arranged in at least one layer. For instance, the device may include multiple layers of particle and binder. In one embodiment, all or a majority of particles in a particular layer may have selected treatment properties, such as type(s) of active agent(s) and/or drug release rate. The particles in layers closer to a surface of the device may be released prior to particles in layers further from the surface. For example, a stent may have struts having layers that run parallel or substantially parallel to a longitudinal axis of the strut.

In other embodiments, properties of the binder may vary spatially in the body structure of the device so as to obtain a selected rate and/or sequence of release of selected particles from the body structure. One embodiment may include varying the erosion rate of the binder by using binder materials with different erosion rates in different portions of the device. For example, the erosion rate of binder may vary by layer.

In another embodiment, the amount of binder may vary spatially in the body structure so as to obtain a selected rate of release of selected particles from the body structure. For example, decreasing/increasing the amount of binder between particles may tend to result in an increase/decrease in the rate of release of particles from the region.

In some embodiments, the device may be configured to disintegrate in a controlled or predictable manner. Selected regions of a body structure may be configured to lose mechanical integrity prior to other regions of the device. The selected regions may have an amount of binder or binder properties that allow the regions to lose mechanical integrity faster.

Additionally, it may be desirable to delay or inhibit erosion of the body structure and release of the particles during a particular period. For example, such a time period may be during the time that a device is being delivered to an implantation site. It may also be desirable to delay erosion and release after implantation to lengthen a time that the device maintains mechanical integrity.

In some embodiments, the device may include an erodible coating above at least some of the particles and binder. "Above" a surface is defined as higher than or over a surface measured along an axis normal to a surface, but not necessarily in contact with the surface. The coating may, for example, be composed of a bioabsorbable polymer. The coating may delay or inhibit exposure to bodily conditions that cause erosion of the particles and binder. Thus, the coating may be configured to delay or inhibit erosion of the body structure of the device and to delay and inhibit release of particles from the body structure.

Various properties of the coating may be used to control the delay of the erosion and release of particles. Erosion rate depends on a number of factors including, but not limited to chemical composition, thickness, porosity, molecular weight, and degree of crystallinity. A thicker coating may tend to take longer to erode, and thus, result in a longer delay of particle release. A more porous coating may increase the erosion rate. In addition, for polymers, molecular weight tends to be inversely proportional to degradation rate. Also, a higher degree of crystallinity tends to result in a lower degradation rate. Thus, amorphous regions of a polymer may tend to have a higher degradation rate than crystalline regions.

In terms of the chemical composition, biodegradable polymers span a continuum from polymers having a relatively constant instantaneous erosion rate with time during a degradation process to polymers with an instantaneous erosion rate that is strongly dependent on time. The former case corresponds to surface eroding polymers, while the latter case refers to bulk eroding polymers. The concepts of surface eroding and bulk eroding are limiting extremes. Real systems typically behave somewhere in between surface erosion and bulk erosion.

As a bulk eroding polymer erodes, a decrease in molecular weight of the polymer can result in deterioration of mechanical properties and contributes to erosion or absorption of the polymer into the bodily fluids. Therefore, the time frame of degradation of a polymer part is dependent on water diffusion, hydrolysis, decrease in molecular weight, and erosion. During a course of treatment with a biodegradable polymeric stent, the polymer degrades resulting in a decrease in the molecular weight of the polymer and deterioration of mechanical properties. Representative examples of bulk eroding polymers include, but are not limited to, poly(L-lactide), poly(glycolide), poly(D,L-lactide), poly(trimethylene carbonate), polycaprolactone, and copolymers thereof.

Alternatively, a surface eroding polymer typically has relatively low water diffusivity. As a result, surface erosion is a heterogeneous process in which degradation and erosion tend to occur at or near a surface of the polymer exposed to the bodily fluids. Representative examples of surface eroding polymers include, but are not limited to, polyorthoesters, polyanhydrides and copolymers thereof.

Additionally, erosion of materials such as biodegradable polymers may also be caused by metabolic or biological activity. Metabolic action is caused particularly by enzyme action leading to significant changes in the chemical structure of a material. Enzymatic degradation of polymers involves cleavage of chemical bonds in the polymer resulting in a scission of the polymer backbone.

Enzymes are proteins or conjugated proteins produced by living organisms and functioning as biochemical catalysts. Thus, enzymatic degradation occurs by a catalytic process. Some enzymes require other enzymes (co-enzymes) to be present in order to be effective, in some cases forming association complexes in which the coenzyme acts as a donor or acceptor for a specific group. Enzymes accelerate the rates of reactions while experiencing no permanent chemical modification as a result of their participation. In some embodiments, a biopolymer sensitive to enzymatic degradation of specific enzymes may be used as a binder, thereby making disintegration an enzyme triggered event. Alternatively, a synthetic binder polymer susceptible to enzymatic cleavage may be used such as a polymer with disulfide bonds.

Furthermore, it may be necessary or desirable to enhance the mechanical stability or integrity of the device. In some embodiments, the device may include a bioabsorbable composite layer above at least some of the particles and binder. The composite layer may also act to delay or inhibit erosion of the binder and release of particles in a manner similar to the coating described above.

As in the coating described above, various properties of the composite layer may be used to control the delay of the erosion and release of particles. The erosion rate of the composite layer depends on the properties of the matrix and the particles.

An embodiment of the composite layer may include a plurality of particles or fibers mixed, dispersed, or embedded with a bioabsorbable matrix. The particles of the layer may include the same or different types of particles held together by the binder in the body structure of the device. The bioabsorbable matrix may include a bioerodible material, such as, a bioabsorbable polymer or bioerodible metal. The bioabsorbable matrix may include the same or different materials as the binder.

In one embodiment, the composite layer may be formed separately from the device. The layer may be formed into a desire shaped and then attached to the device. For example, a layer for a stent may be in the shape of a tube. The layer may be formed by various methods, such as, extrusion or injection molding. A mixture of the matrix material and the particles may be extruded or molded into the desired shape.

In addition, the layer may be attached to the device in a number of ways. For example, at least a portion of the bioabsorbable matrix may be dissolved by a solvent at a surface of the layer. Alternatively or additionally, at least a portion of the binder may be dissolved by a solvent. The dissolved surfaces may then be joined and the solvent removed by evaporation or by heating.

In another embodiment, a composite layer may be formed by applying a fluid including a solvent, a bioabsorbable polymer, and particles or fibers to the device. The solvent may then be removed by evaporation or heating, leaving a composite layer of bioabsorbable polymer and particles over the device.

There are various embodiments of forming the implantable medical device, described herein. In some embodiments, the particles may be preformed and then incorporated into the binder material. In certain embodiments, a method may include applying a fluid on a predefined portion of a plurality of particles. In one embodiment, the particles may be disposed in the shape of the device. In the case of a stent, the particles may be disposed on a mandrel, for example. In some embodiments, the particles may be formed into the shape of a tube, sheet, or a stent by sintering, for example. In other embodiments, the particles may be disposed on a polymeric or metallic substrate or scaffolding in the shape of the device.

Additionally, the method may further include allowing the fluid to releasably bind together the predefined portion of particles with a binder to form a layer which includes the particles bound together with the binder. The particles not bound by the binder may be removed.

In one embodiment, the applied fluid may include a binder dissolved in a solvent in which the binder has a relatively high solubility. Thus, after removal of all or substantially all of the solvent, binder may be left behind which binds together the predefined portion of particles. In an embodiment, it is desirable for the particles to have a relatively low or no solubility in the solvent. Representative examples of solvents that may be used include chloroform, acetone, chlorobenzene, ethyl acetate, 1,4-dioxane, ethylene dichloride, 2-ethyhexanol, ethanol, methanol, and combinations thereof. The solvent and materials for the binder and the particles may be selected so that the binder and particles have a desired solubility in the solvent.

In another embodiment, the applied fluid may include a solvent that dissolves a portion of the predefined portion of particles. Removal of all or substantially all of the fluid allows the dissolved portion of the particles to bind the predefined portion of particles together. In addition, additional layers of particles and binder may be applied in a similar manner. As discussed above, the particles and binder may be different in different layers.

In one embodiment, stereolithography may be used in fabricating the device. "Stereolithography" or "3-D printing" refers to a technique for manufacturing solid objects by the sequential delivery of energy and/or material to specified points in space to produce that solid. The manufacturing process may be controlled by a computer using a mathematical model created with the aid of a computer. In the case of fabricating an implantable medical device, the fluid may be applied by an applicator, such as a nozzle, programmed to apply the fluid in a pattern corresponding to the predefined portion of particles. The pattern may be based on computer-generated construct of the device.

In certain embodiments, a fluid applicator may be configured to apply an amount and types of binder to obtain a desired rate of erosion and selected rate and/or sequence of release of selected particles from the body structure. For example, a greater amount of fluid may be applied to selected particles to increase the degree of binding between the particles which may tend to decrease rate of release of particles and disintegration of the device.

In further embodiments, the implantable medical device may be fabricated by forming a coating including the plurality of particles bound together with the binder on a polymeric or metallic substrate or scaffolding. In one embodiment, a coating may be formed by applying fluid that includes a solvent, a bioabsorbable polymer, and particles. The solvent may then be removed by evaporation or heating, leaving a coating including the bioabsorbable polymer and particles over the device.

In further embodiments, the implantable medical device may be fabricated by applying a suspension of particles on a polymeric or metallic substrate or scaffolding. The suspension may include particles, a solvent, and a bioabsorbable polymer. After applying the suspension, the solvent may then be removed by evaporation or heating, leaving the bioabsorbable polymer and particles. The particles may be bound together by the bioabsorbable polymer which acts as a binder. The particles and/or binder may include active agents. In some embodiments, additional layers may be formed by repeated application of suspension and removal of solvent.

In other embodiments, the particles may be formed by self-assembly within the binder material. For example, an amphiphilic block copolymer may be mixed with a hydrophilic binder in an aqueous solution. Amphiphilic molecules may then self-assemble to form particles. Representative examples of amphiphilic block copolymers include, but are not limited to poly(ethylene glycol)-poly(lactic acid); poly (ethylene glycol)-poly(caprolactone); poly(vinylpyrrolidone)-poly(lactic acid). Representative examples of hydrophilic binders include, but are not limited to, poly(ethylene glycol), poly(vinylpyrrolidone), and poly(vinyl acetate). Syed, David, please comment. In some embodiments, crosslinkers may be conjugated onto the particle-forming block-copolymers. The particles may be further stabilized by crosslinker activation after the formation of the particle and binder matrix.

Representative examples of polymers that may be used for binder and/or particles to fabricate embodiments of implantable medical devices disclosed herein include, but are not limited to, poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrin glue, fibrinogen, cellulose, starch, collagen and hyaluronic acid, elastin and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating embodiments of implantable medical devices disclosed herein include ethylene vinyl alcohol copolymer (commonly known by the generic name EVOH or by the trade name EVAL), poly(butyl methacrylate), poly(vinylidene fluoride-co-hexafluoropropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, poly(vinyl acetate), styrene-isobutylene-styrene triblock copolymers, and polyethylene glycol.

Representative examples of biosoluble materials that may be used for a binder and/or particles to fabricate embodiments of implantable medical devices disclosed herein include, but are not limited to, poly(ethylene oxide); poly(acrylamide); poly(vinyl alcohol); cellulose acetate; blends of biosoluble polymer with bioabsorbable and/or biostable polymers; N-(2-hydroxypropyl)methacrylamide; ceramic matrix composites; and tyrosine based polycarbonates.

A non-polymer substrate of the device may be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. The substrate or coating for a device may also be made partially or completely from a purified biodegradable, bioabsorbable, or biostable polymer.

As indicated above, the particles and the binder may include active agent(s) such as anti-inflammatories, antiproliferatives, and other bioactive agents.

An antiproliferative agent can be a natural proteineous agent such as a cytotoxin or a synthetic molecule. Preferably, the active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin $I_1$, actinomycin $X_1$, and actinomycin $C_1$), all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives include 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin (ABT-578 manufactured by Abbot Laboratories, Abbot Park, Ill.), prodrugs thereof, co-drugs thereof, and combinations thereof. In one embodiment, the anti-proliferative agent is everolimus.

An anti-inflammatory drug can be a steroidal anti-inflammatory agent, a nonsteroidal anti-inflammatory agent, or a combination thereof. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof. In one embodiment, the anti-inflammatory agent is clobetasol.

Alternatively, the anti-inflammatory may be a biological inhibitor of proinflammatory signaling molecules. Anti-inflammatory biological agents include antibodies to such biological inflammatory signaling molecules.

In addition, the particles and binder may include agents other than antiproliferative agent or anti-inflammatory agents. These active agents can be any agent which is a therapeutic, prophylactic, or a diagnostic agent. In some embodiments, such agents may be used in combination with antiproliferative or anti-inflammatory agents. These agents can also have anti-proliferative and/or anti-inflammmatory properties or can have other properties such as antineoplastic, antiplatelet, anti-coagulant, anti-fibrin, antithrombonic, anti-mitotic, antibiotic, antiallergic, antioxidant, and cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax a (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl(4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, and genetically engineered epithelial cells. The foregoing substances are listed by way of example and are not meant to be limiting.

Other bioactive agents may include antiinfectives such as antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary; peripheral and cerebral; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents. Other active agents which are currently available or that may be developed in the future are equally applicable.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. An implantable medical device consisting of:
a body structure consisting of erodable particles and an erodable binder releasably binding the particles together such that after implantation the binder erodes to release the particles, wherein the particles have a slower erosion rate than the binder, and wherein the particles are dispersed in the binder,
wherein the particles consist of a bioerodable polymer and an active agent, wherein the bioerodable polymer acts as a carrier of the active agent,
wherein the binder consists of a bioabsorbable polymer,
wherein the bioerodable polymer comprises a polymer selected from the group consisting of poly(ethylene oxide), poly(acrylamide), acrylic polymers and copolymers other than polyacrylates, poly(vinyl alcohol), tyrosine based polycarbonates, cellulose acetate, and polyethylene glycol; and
optionally a coating over the body structure consisting of a coating polymer and a drug,
wherein the device is a stent adapted to be implanted in a bodily lumen.

2. The device of claim 1, wherein erosion is due to dissolution, chemical breakdown, and/or enzymatic degradation of the binder and/or particles.

3. The device of claim 1, wherein rheological forces facilitate release of the particles from the binder.

4. The device of claim 1, wherein at least some of the released particles are adapted to be transported to a selected bodily region distal from a local region of implantation and to treat the distal region with the active agent.

5. The device of claim 4, wherein the local region comprises a vascular region comprising a lesion and the distal region comprises vasculature distal from the lesion and/or a per-adventitial region.

6. The device of claim 1, wherein the particles do not undergo substantial erosion prior to being released from the binder.

7. The device of claim 1, wherein the active agent is encapsulated, embedded, or dispersed within the bioerodable polymer.

8. The device of claim 1, wherein at least an amount of the active agent is configured to be released from the bioerodable polymer prior to the particles being released from the binder so at to locally administer the active agent at or near a region where the device is implanted.

9. The device of claim 1, wherein the active agent is coated on the bioerodable polymer.

10. The device of claim 1, wherein the size of the particles is on a nano-scale or micro-scale.

11. The device of claim 1, wherein the particles comprise an outer shell and an inner compartment comprising the active agent.

12. The device of claim 1, wherein the active agent is released subsequent to the release of the particles from the binder.

13. The device of claim 1, wherein the particles are released upon the degradation of the binder of the body structure, the body structure being a scaffolding that is the primary source of structural support.

14. A stent consisting of:
a scaffold consisting of particles and an erodable binder releasably binding the particles together such that after implantation the binder erodes to release the particles, wherein the particles have a slower erosion rate than the binder, wherein the particles are dispersed in the binder, and wherein the particles consist of an active agent and an amphiphilic block copolymer and the binder consists of a hydrophilic polymer, wherein the amphiphilic block copolymer acts as a carrier of the active agent; and
optionally a coating over the scaffold consisting of a coating polymer and a drug.

15. The stent of claim 14, wherein the amphiphilic block copolymer is selected from the group consisting of poly(ethylene glycol)-poly(lactic acid), poly(ethylene glycol)-poly(caprolactone), and poly(vinylpyrrolidone)-poly(lactic acid).

16. The stent of claim 15, wherein the hydrophilic polymer is selected from the group consisting of poly(ethylene glycol), poly(vinylpyrrolidone), and poly(vinyl acetate).

17. A stent consisting of:
a scaffold consisting of particles and an erodable binder releasably binding the particles together such that after implantation the binder erodes to release the particles, wherein the particles have a slower erosion rate than the binder, wherein the particles are dispersed in the binder, and wherein the particles consist of an active agent and micelles consisting of amphipathic molecules having both hydrophobic and hydrophilic groups, wherein the binder consists of a bioabsorbable polymer, wherein the micelles act as a carrier of the active agent, wherein the amphipathic molecules are arranged in a cluster having a spherical, cylindrical, or discoidal shape; and
optionally a coating over the scaffold consisting of a coating polymer and a drug.

18. The stent of claim 17, wherein the micelles are stabilized by crosslinking of the amphipathic molecules that form the micelles.

19. A stent consisting of:
a scaffold consisting of particles and an erodable binder releasably binding the particles together such that after implantation the binder erodes to release the particles, wherein the particles have a slower erosion rate than the binder, wherein the particles consist of an active agent and vesicles consisting of block copolymers or lipids, wherein the vesicles act as a carrier for the active agent; and
optionally a coating over the scaffold consisting of a coating polymer and a drug.

20. The stent of claim 19, wherein the vesicle comprises a shell formed by at least one lipid bilayer and an enclosed compartment.

21. The stent of claim 20, wherein the vesicle is stabilized by crosslinking of the lipid bilayer shell.

22. The stent of claim 19, wherein the active agent is loaded in an enclosed compartment of the vesicle.

* * * * *